United States Patent [19]
Greenwald et al.

[11] Patent Number: 5,158,766
[45] Date of Patent: Oct. 27, 1992

[54] STORAGE STABLE AQUEOUS SOLUBLE GERMICIDAL FILM FORMING COMPOSITION

[75] Inventors: Richard B. Greenwald, Eagan; David A. Halsrud, Minneapolis, both of Minn.

[73] Assignee: Ecolab, Inc., St. Paul, Minn.

[21] Appl. No.: 545,768

[22] Filed: Jun. 28, 1990

Related U.S. Application Data

[63] Continuation of Ser. No. 337,336, Apr. 13, 1989, abandoned.

[51] Int. Cl.$^5$ ............................................. A61K 31/74
[52] U.S. Cl. .................. 424/78.33; 424/78.37
[58] Field of Search ............ 424/78, 80, 81, 78.33, 424/78.37

[56] References Cited

U.S. PATENT DOCUMENTS

| | | | |
|---|---|---|---|
| 2,931,753 | 4/1960 | Chesbro et al. | 167/22 |
| 2,984,639 | 5/1961 | Stamberger et al. | 260/32.4 |
| 3,163,602 | 12/1964 | Lindblom et al. | 252/8.8 |
| 3,590,118 | 6/1971 | Conrady et al. | 424/405 |
| 3,749,772 | 7/1973 | Cardorelli et al. | 424/81 |
| 4,126,563 | 11/1978 | Barber | 424/404 |
| 4,479,840 | 10/1984 | Takegawa et al. | 156/327 |
| 4,501,834 | 2/1985 | Su | 524/28 |
| 4,696,677 | 9/1987 | Colegrove et al. | 44/51 |
| 4,783,340 | 11/1988 | McDonell et al. | 427/2 |

OTHER PUBLICATIONS

"Precipitation Phenomena in Mixtures of Anionic and Cationic Surfactants in Aqueous Solutions" by Stellner et al.

*Primary Examiner*—Thurman K. Page
*Assistant Examiner*—Peter F. Kulkosky
*Attorney, Agent, or Firm*—Merchant, Gould, Smith, Edell, Welter & Schmidt

[57] ABSTRACT

A single-part aqueous, storage stable, antimicrobial film-forming composition comprising a major portion of water, an antimicrobially effective amount of a cationic germicidal agent having the structure $(R)(R_1)(R_2)(R_3)N^+ X^-$, wherein R, $R_1$, $R_2$, and $R_3$ are independently selected from groups including benzyl, alkyl, benzyl, halo benzyl, $C_{1-14}$ alkyl, $C_{5-24}$ alkyl or $C_{1-4}$ hydroxyalkyl and $X^-$ represents an anion capable of imparting water solubility or dispersability to the compound, and a stoichemetrically effective amount of acid functional anionic polymer, wherein said cationic germicidal agent and anionic polymer remain dissolved as a homogeneous aqueous solution until used.

46 Claims, 2 Drawing Sheets

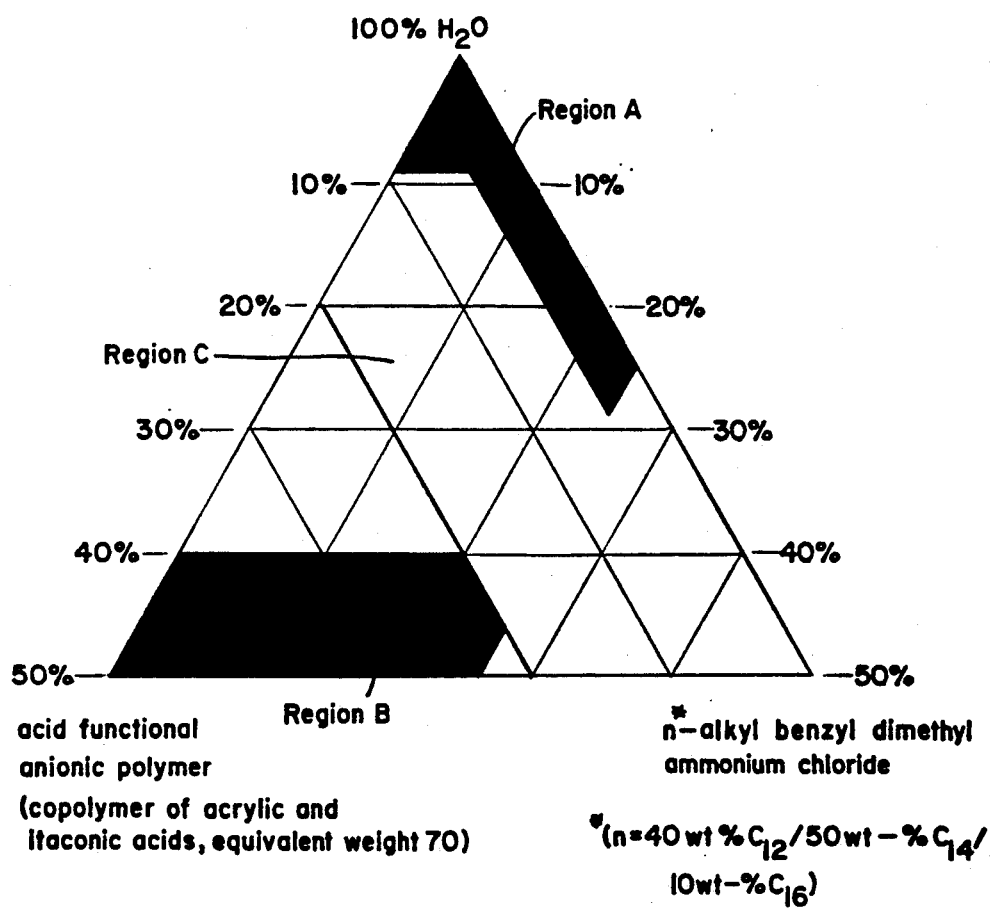

5,158,766

STORAGE STABLE AQUEOUS SOLUBLE GERMICIDAL FILM FORMING COMPOSITION

This is a continuation of application Ser. No. 07/337,336, filed Apr. 13, 1989, now abandoned.

FIELD OF THE INVENTION

The invention relates generally to antimicrobial film-forming compositions for the hospitality and health care industries as well as the institutional food processing industries including the dairy and food packaging industries. More particularly, the present invention relates to an aqueous film-forming composition which prior to application remains storage stable in a homogeneous solution and once applied, forms a film having antimicrobial character.

BACKGROUND OF THE INVENTION

The benefits of antimicrobial films is well established in certain fields, such as the health care industry and the food processing industry. The application of germicidal or sanitizing polymeric films having limited water solubility to a hard porous or nonporous surface often provides the necessary protection from contamination by any number of environmental bacterial or viral elements.

However, while the state of antibacterial films has evolved, there is limited versatility and variability in the films currently available for use. For instance, U.S. Pat. No. 2,984,639 to Stamberger et al provides for a cast polymeric antimicrobial film formed in situ from a two film-forming solutions having no one-part intermediate aqueous film-forming compositional phase.

While precipitate germicidal films such as that disclosed in Stamberger have been developed, the versatility of these films due to their limited solubility has been well documented. For example, U.S. Pat. No. 2,931,753 to Chesbrow provides an inorganic ammonium salt of a polysaccharide carboxylic acid having a limited solubility even in organic solvents. The Chesbrow composition, in fact, is soluble only to about 1% and then only in methanol. However, even a film-forming composition based in an organic solvent presents certain limitations to the health care and food processing industries due to the inherent toxicity and flammability of many organic solvents.

Some progress has been made in providing antimicrobial films from an aqueous carrier, as seen by U.S. Pat. No. 4,783,340 to McDonell et al. However, to avoid premature precipitation the McDonnell et al composition requires that the anionic polymer and quaternary constituents be stored separately and, further, applied only through a dual-head spray unit.

SUMMARY OF THE INVENTION

The present invention provides an aqueous storage stable antimicrobial film-forming composition capable of imparting a disinfecting or sanitizing character to a hard porous or nonporous surface. Surprisingly, the film-forming composition of the present invention allows for a homogeneous, storage stable mixture of a bactericidal cationic quaternary ammonium chloride and an acid functional anionic polymer in an aqueous carrier without need for a solubilizing organic solvent.

The aqueous composition of the present invention remains precipitate-free and phase stable throughout storage. Once deposited on the surface of application, the film-forming composition provides a germicidal film from the aqueous solvent which adheres to the surface of application. The resulting film combines a scrub resistance with a renewable antimicrobial property. Heretofore such an antimicrobial film imparted from a storage stable aqueous composition was unknown.

The film forming composition of the present invention comprises water, an antimicrobially effective amount of a cationic germicidal agent, and an amount of acid functional anion, wherein the concentration of the anion and cation are adjusted so that when in solution, the composition remains precipitate-free and phase stable until deposited upon the surface of application.

BRIEF DESCRIPTION OF THE DRAWINGS

FIGS. 1 and 2 depict the solubility profiles of exemplary embodiments of the composition of the present invention.

DETAILED DESCRIPTION OF THE INVENTION

Figure 1:
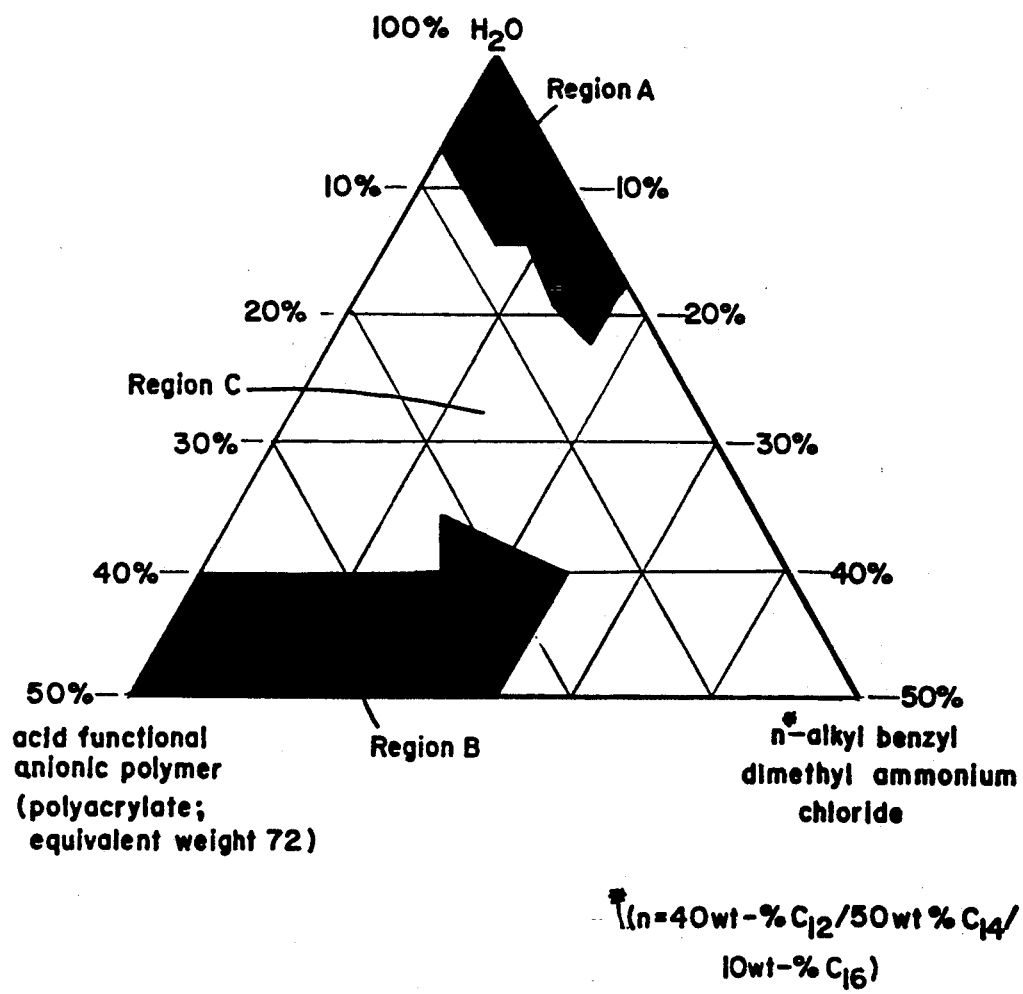

The present invention is a film-forming composition comprising a cationic antimicrobial agent and an acid functional anionic polymer. Optionally, the composition may also comprise film adjuvants such as coalescing agents or thickeners or other materials which provide a film having a smooth surface or texture.

Cationic Germicidal Agent

The cationic germicidal agent used in the present invention functions to provide the necessary antimicrobial action and to facilitate the precipitation of a compositional film upon the surface of application. Generally, the cationic germicidal agent used should be susceptible to dissolution in an aqueous solvent and not subject to degradation, precipitation, or phase separation over extended periods of time when stored in this compositional form.

A wide variety of cationic germicidal agents may be included in effective amounts without inducing undesirable interactions or chemical reactions between the major components of the compositions. Preferred germicidal agents are quaternary ammonium compounds having the structure $(R)(R_1)(R_2)(R_3)N^+X^-$ wherein R, $R_1$, $R_2$, and $R_3$ are independently selected from the groups including benzyl, alkyl benzyl, halo benzyl, $C_{1-14}$ alkyl, $C_{5-24}$ alkyl or $C_{1-4}$ hydroxyalkyl, and $X^-$ represents an anion capable of imparting water solubility or dispersibility. Such anions include chloride, bromide, iodide, sulfate, methylsulfate, and others.

In somewhat greater detail, R, $R_1$, $R_2$, and $R_3$ can be selected from moieties including alkyl, for example methyl, ethyl, propyl, or butyl; substituted alkyl, for example, hydroxyethyl, or hydroxypropyl; cycloalkyl moieties, for example cyclohexyl; aryl, including phenyl, naphthyl, etc.; aralkyl moieties, for example benzyl, substituted benzyl, etc.; alkaryl moieties, for example tolyl, xylyl, alkylnaphthyl; $C_{6-24}$ higher alkyl moieties including hexyl, 2-ethylhexyl, octyl, isooctyl, pentyl, dodecyl, tetradecyl, icosyl, etc.

Preferred quaternary ammonium compounds for use in this sanitizing compositions of the invention include a $C_{6-24}$ alkyl dimethylbenzyl ammonium chloride and dimethyl dichlorobenzyl ammonium chloride.

Acid Functional Anionic Polymers

The second essential element of the composition of the present invention is an acid functional anionic polymer. Once the film-forming composition is applied to the intended surface, the acid functional anionic polymer interacts with the cationic germicidal agent to form an aqueous insoluble antimicrobial film.

This aqueous insoluble or hydrophobic character assists in imparting a certain amount of abrasion or scrub resistance to the cast film composition. Optimally, the acid functional anionic polymer should be aqueous soluble at certain concentrations, capable of forming a film with the cationic germicidal agent and compatible with the cationic germicidal agent used in the composition. In other words, the acid functional anionic polymer should not mask, neutralize, or degrade the germicidal character of the antimicrobial film once formed. Film properties such as adhesion, clarity, scrub resistance and the aqueous solubility of the composition prior to application can be altered by varying the concentration and type of the acid functional anionic polymer in the composition.

The water insoluble sanitizing films of the invention are formed in an interaction between a cationic germicidal agent and an acid functional anionic polymer once the composition is applied to the intended surface. By acid functional anionic polymer we mean a polymer with a pendent acid group such as a pendent carboxyl group, a pendent sulfonic acid group or other acid groups.

Preferred acid functional anionic polymers are typically polymeric compositions having pendent carboxyl groups that are completely water soluble or partially water soluble. If not already, the polymers are made soluble when neutralized by a basic reactant. Water solutions of the substantially neutralized acid functional anionic polymer are prepared and then intermixed with the cationic germicidal agent to form the homogeneous solution of the invention.

We have found that the preferred sanitizing films of this invention can be made from (i) a homopolymer polymer made from an ethylenically unsaturated carboxylic acid containing monomer or (ii) a copolymer made from a monomer mixture containing an ethylenically unsaturated carboxylic acid containing monomer or (iii) a mixture of homopolymers and/or copolymers. Exemplary polymers are those composed of the ammonium salt of polyacrylate monomers or a mixture of acrylate and itaconic monomers. These polymers have a molecular weight ranging from about 4,000 to 20,000 with an equivalent weight ranging from about 50 to 150.

Alternatively, the sanitizing films of the present invention can be made by reacting a quaternary ammonium compound with a polymer having pendent acid groups other than a carboxylic acid. Such pendent groups can include sulfonic acid groups, phosphonic acid groups, etc. Such polymers can be made by forming homopolymers or copolymers by polymerizing a mixture of monomers containing monomers having sulfonic acid groups, phosphonic groups, etc. Examples of monomers having pendent sulfonic acid groups include vinyl benzene sulfonic acid, acrylamidoalkyl sulfonic acid, ethylenically unsaturated olefin sulfonic acid, and others well known to the skilled artisan.

The acid functional polymer preferably is a homopolymer or copolymer containing an ethylenically unsaturated carboxylic acid containing monomer. Such ethylenically unsaturated carboxylic acid containing monomers include methacrylic acid, acrylic acid, itaconic acid, aconitic acid, cinnamic acids, crotonic acids, mesaconic acids, maleic acid, fumaric acid, etc. The carboxylic acid functional copolymer can contain other ethylenically unsaturated monomers compatible with the ethylenically unsaturated carboxylic acid containing monomers disclosed above. Such monomers include ethylene, propylene, isobutylene, vinyl chloride, vinyl acetate, styrene, chlorostyrene, and others well known to the polymer chemist. Further, the polymers can contain hydrophilic ethylenically unsaturated monomers having amino groups, hydroxyl groups, ether groups, ester groups, and others. Preferred carboxylic acid functional polymers are homopolymers of acrylic acid or methacrylic acid or copolymers containing acrylic acid or methacrylic acid and a second carboxylic acid containing monomer selected from the group consisting of itaconic acid, maleic acid or anhydride wherein in the copolymer the molar ratio between the acrylic monomer and the second monomer is about 1-5 moles of acrylic monomer per each mole of second monomer.

Alternatively the carboxylic acid functional polymer can be a polysaccharide having pendent carboxylic acid groups. Examples of such polysaccharide carboxylic acid functional polymers include carboxymethyl cellulose and carboxylethyl cellulose, carboxymethyl starch and carboxyethyl starch, alginic acid and alginic acid derivatives, pectic acid or similar natural and synthetic carboxylic acid derivatives of a polysaccharide.

Adjuvants

The aqueous storage stable antimicrobial film-forming composition of the present invention may also contain other film adjuvants such as thickeners or leveling agents. Principally, these optional ingredients are intended to serve an aesthetic function by thickening or smoothing the film after application. More viscous films will, once applied, be less likely to run when applied to surfaces which are vertical or at an angle which is less than horizontal. Moreover, a thickener or leveling agent will tend to provide a film which does not streak or ripple when applied to the intended surface of application.

Generally, any water soluble thickener or leveling agent will have utility with the present invention. Thickeners such as alkaline and alkaline earth metal salts of carboxymethyl cellulose, alginates, and polycarboxylates such as those available from B. F. Goodrich Co. under the trade, name Carbopol ® are all useful in the present invention.

Thickener concentration may generally vary from 0% to 10%, and preferably from 0.5% to 5% and most preferably from 0.5% to 3.0% of total composition weight. The amount of thickener will vary depending upon the properties to be imparted to the film-forming composition as well as the resulting film. For instance, varying the amount of thickener may affect thickness and adhesion of the resulting film as well as the viscosity and dispensing rate of the film-forming composition.

Leveling or coalescing agents such as propylene glycol, butoxyethanol, and alkyl glycol ethers such as diethylene glycol monobutyl ether, ethylene glycol monobutyl ether, diethylene glycol monomethyl ether, propylene glycol monopropyl ether, ethylene glycol monopropyl ether, and ethylene glycol monoethyl ether acetate as well as other water miscible glycol ethers or glycol ether esters are useful in the composition of the present invention.

The concentration of coalescing agents present in the film-forming composition generally affects the aesthetic character of the resulting film. For instance, varying the amount of coalescing agent may alter the amount of pitting, roughness, or unevenness in the resulting film. However, the use of too great a concentration of coalescing agent may increase the flammability of the film. Generally, a coalescing agent may be used in a concentration ranging from 0% to 15%, and preferably from 0% to 10%, and most preferably from 0.5% to 5% of the total composition weight.

Formulation Concentrations

Generally, the composition of the present invention is composed of three constituents being an aqueous carrier at greater than 50 wt-% of the composition, a polymeric anionic constituent being less than 50 wt-% of the composition of the present invention, and a cationic germicidal agent which will also be less than 50 wt-% of the composition. The only limitation upon the concentration of these various constituents is that the film-forming composition of the present invention be precipitate-free and homogeneous prior to its use on the intended surface of application.

Taking each of the constituents in turn, varying the concentrations within the foregoing ranges will provide various qualities to the composition of the present invention.

Increasing the concentration of cationic germicidal agent will provide an initial germicidal effect to the resulting film which will eliminate any microbial elements present at the time and place of application. The use of a higher concentration of cationic germicidal may also provide some residual tack to the surface of the film which can be extinguished by an aqueous washing. Using an increased concentration of the acid functional anionic polymer will create the same tacky effect in the film which can be extinguished through an aqueous washing. In turn, the thickness of the film controls the effective germicidal impact which the film will have, i.e. the thicker the film, the longer it will last providing a germicidal effect on the surface of application given relative use conditions such as abrasion and washing.

From our research, we believe that the cationic germicidal agent and the acid functional anionic polymer interact in a stoichiometric ratio of 1:1 on a per charge basis. Accordingly, as will be exemplified below, the concentration of the two primary constituents in the film-forming composition may vary broadly. Preferably, however, the constituent concentrations will equate to provide a 1 to 1 equivalence ratio of cationic and anionic charge. This concentration range will avoid waste of either constituent and provide a film surface having minimum tack with the appropriate germicidal efficacy.

Generally, the concentration of a cationic germicidal constituent and the acid functional anionic polymer are exemplified FIGS. 1 and 2 with a primary limitation being that in all instances the composition of the present invention will be storage and phase stable in an aqueous solution.

As can be seen from FIG. 1, this exemplary embodiment of the composition of the present invention comprises a major portion of 50% or more water. Generally speaking, the composition of the present invention must contain at least 50% water to remain storage and phase stable. Exemplary composition of FIG. 1 also comprises at least about 8 wt-% of polyacrylate to 40 wt-% polyacrylate having an equivalent weight of 72. As a final constituent of exemplary composition of the present invention shown in FIG. 1 comprises 1 wt-% to about 50 wt-% of a cationic germicidal constituent being alkyl benzyl dimethyl ammonium chloride (50 wt-% $C_{14}$/40 wt-% $C_{12}$/10 wt-% $C_{16}$).

The concentration ranges of these composition constituents may vary freely within these ranges as represented by Region C of FIG. 1. However, the constituent concentrations cannot vary into Region A or Region B. Regions A and B are areas of aqueous insolubility where the composition will either separate into two phases or precipitate within the aqueous carrier. Region C, being the area free of cross-hatching, represents the area within which this exemplary embodiment of the composition of the present invention is phase stable and lacking in precipitate.

FIG. 2 shows a similar exemplary embodiment of the composition of the present invention. This exemplary composition of the present invention has a major portion or at least 50% more water. The exemplary composition of the present invention shown in FIG. 2 also comprises from about 1 wt-% to 50 wt-% an alkyl benzyl dimethyl ammonium chloride (50 wt-% $C_{14}$/40 wt-% $C_{12}$/10 wt-% $C_{16}$). As a final constituent, the exemplary composition of the present invention shown in FIG. 2 comprises from about 10 wt-% to 40 wt-% of a copolymer of itaconic and acrylic acids, having an equivalent weight of about 70. As can be seen in FIG. 2, this exemplary composition of the present invention may have constituent concentrations which can be found in Region C where the composition will be a phase stable precipitate aqueous solution. However, here again, the exemplary composition of the present invention cannot have constituent concentrations which will fall into either Region A or Region B, being representative of concentrations where the composition of the present invention is not phase stable or precipitate-free.

Generally, the composition of the present invention may be formulated by adding the acid functional anionic polymer to a mixing unit charged with water. The polymer is then neutralized with $NH_4OH$ to create the ammonium salt of the polymer. The cationic germicidal agent is then carefully added to the composition. Once mixed, the sanitizing composition of the present invention can be sprayed from a single volumetric storage container through a single spray nozzle providing a spray pattern whereby the composition is directed generally over the application surface.

The sanitizing film-forming composition of the present invention can be used in household, or industrial and institutional settings. However, the compositions of the invention are preferred for use in industrial and institutional areas where sanitizing activity is critical and large surface areas exist which require the rapid efficient application of the sanitizing film. The compositions of this invention are particularly suited to sanitize hard surfaces such as piping, ceramic tile, concrete floors and walls, glass and metal equipment surfaces, flexible plastic functional equipment, covers, and wood surfaces. The compositions of this invention may also be used on painted surfaces, food processing tanks, and in drain and run-off areas.

Generally, the coating process is continued to the extent that the amount of sanitizing film delivered to the surface is that required to form an integral uniform polymeric film. The film should contain about $10^{-3}$ to 10 milligrams, preferably $10^{-2}$ to 1.0 milligrams of the quaternary ammonium complex salt film-forming composition, depending on the molecular weight of the quat, per square centimeter surface to be treated. Additional amounts of the film can be added to an applied film in order to provide higher levels of sanitizing or to renew film integrity at an existing application. Further, the films formed in the application can be augmented by additional applications of sanitizing compositions over time. At such time that the surface requires cleaning or that the surface appears to have lost its sanitizing properties, the films of the invention can be removed by treatment with dilute concentrations of organic or inorganic acids such as HCl acid, sulfuric acid, or acetic acid, among others.

As the composition of the present invention provides a storage stable homogeneous aqueous mixture of cationic germicidal agent and acid functional polymeric anion in a aqueous solution, the composition may be applied through any variety of means including brushing, dipping, or rolling. Preferably, the composition of the present invention is applied by spray application through a single nozzle spray applicator such as a manual or pressurized aerosol sprayer.

WORKING EXAMPLES

Following below are formulatory, stability, application and microbiological working examples using the composition of the present invention.

FORMULATORY EXAMPLE I 320 grams of 50% itaconic/acrylic acid copolymer (about 1:3 mole ratio) was diluted to a total of 1600 grams with distilled water. Concentrated ammonium hydroxide (110 grams) was added to the mix until the pH was 8. While stirring carefully, 840 grams of 50% active quaternary alkyl dimethyl benzyl ammonium chloride (40% $C_{12}$, 50% $C_{14}$, 10% $C_{16}$) was added to the solution.

FORMULATORY EXAMPLE II 100 grams of 50% actives polyacrylic acid was diluted with 400 grams with distilled water. Concentrated ammonium hydroxide was added to the mix until the pH was 8 then distilled water was added until the total weight is 500 grams. 500 grams of a 20% actives quaternary alkyl dimethyl benzyl ammonium chloride was then carefully added to the solution.

FORMULATORY EXAMPLE III 16.0 grams of 50% active itaconic/acrylic acid (about 1:3 mole ratio) copolymer was diluted to a total of 80 grams with distilled water. Concentrated ammonium hydroxide was then added to the mix until the pH was 8. 6.4 grams of a sodium alginate thickener known as Kelgin XL was added to the mix with stirring until a homogeneous paste was obtained. While stirring, 84 grams of a 50% actives quaternary alkyl dimethyl benzyl ammonium chloride (40% $C_{12}$, 50% $C_{14}$, 10% $C_{16}$) was slowly added solution. The resulting viscous material could be brushed on surfaces.

STABILITY EXAMPLE 160 grams of 50% itaconic/acrylic acid copolymer (about 1:3 mole ratio) was diluted to 800 grams with distilled water. Concentrated $NH_4OH$ was added to the mix until the pH was about 8.

840 grams 50% active quaternary alkyl/dimethyl benzyl ammonium chloride (40% $C_{12}$, 50% $C_{14}$ and 10% $_{16}$) was added dropwise and stirred into the solution over a period of several hours. A stable, clean, but slightly yellow solution resulted.

This homogeneous solution was examined and found to be precipitate-free and phase stable after 20 months.

Antimicrobial Efficacy

A study of the sanitizing efficacy of the composition of the present invention was undertaken using the Formulatory Examples which were previously prepared.

The term "sanitizing", as used herein, is defined in the Environmental Protection Agency's "Pesticide Assessment Guidelines" subdivision G: Product Performance 1982, Section 91-2 (j)2. The product shows at least a 99.9% (3 log) reduction in the number of the test microorganisms over a parallel control count.

The purpose of this test was to evaluate the efficacy of homogeneous solutions treated tiles when challenged with a bacterial inoculation. Tiles were treated with homogeneous solutions of Formulatory Examples I and III determine sanitizing efficacy.

While stirring 950 grams of Formulatory Example I, 105 grams of butoxyethanol coalescing agent were added to the mix. An air sprayer set at 20 psi was used to apply, Formulatory Examples I by making two passes over the tiles. The tiles were allowed to dry for 30 minutes and then another two passes was made with the sprayer. The tiles were allowed to air dry at least 24 hours before measuring sanitizing activity.

Formulatory Example III was applied by swabbing the composition onto the tiles where it was then allowed to dry for at least 24 hours.

The tiles were showered for various lengths of time with deionized water as indicated in Table I. Two untreated tiles were used as controls.

The tiles were inoculated with one ml 24 hour culture of *S. aureus* which was spread over entire tile and given a contact time of precisely 15 minutes. At 15 minutes survivors were recovered from the tiles by wiping with a sterile moist 1"×1" swatch which were immediately placed in 10 ml letheen broth to neutralize the quaternary.

Surviving *S. aureus* transferred to the Letheen broth were enumerated by standard plate count methods. Plates were incubated at 30° C. and then counted.

TABLE I

| | Log Reduction of Colony Forming Units (CFU's)* | | | |
|---|---|---|---|---|
| | Shower Time | | | |
| | 0 min. | 15 min. | 30 min. | 60 min. |
| Formulatory Example I | 6.0 | 6.0 | 6.0 | — |
| Formulatory Example III | 6.7 | 5.0 | — | 4.1 |

*Microbiological colony forming unit = CFU of *S. aureus*

After the resulting films had been subjected to an aqueous shower of up to 60 minutes in length, the results showed greater than a 3 log reduction (99.9%) of the inoculation in both Formulatory Examples I and III.

We claim:

1. A single-part homogeneous, solvent-free, aqueous, storage stable, antimicrobial film-forming composition comprising:
   (a) a major portion of water;
   (b) an antimicrobially effective amount of a cationic germicidal agent having the structure (R) ($R_1$) ($R_2$) ($R_3$) N+X−;

wherein R, R$_1$, R$_2$, and R$_3$ are independently selected from groups including benzyl, alkyl benzyl, halo benzyl, C$_{1-14}$ alkyl, C$_{5-24}$ alkyl or C$_{1-4}$ hydroxyalkyl and X$^-$ represents an anion capable of imparting water solubility or dispersability to the compound; and (c) a stoichemetrically effective amount of acid functional anionic polymer, wherein said germicidal agent and anionic polymer remain dissolved in a homogeneous aqueous solution until used.

2. The composition of claim 1 wherein at least one of R, R$_1$, R$_2$, and R$_3$ moieties on the cationic germicidal agent compound is independently selected from the group consisting of methyl, ethyl, propyl, and butyl.

3. The composition of claim 1 wherein at least one of the R, R$_1$, R$_2$, and R$_3$ moiety of the cationic germicidal agent is independently selected from the group consisting of cycloalkyl groups, aryl groups, aryl alkyl groups, and higher alkyl groups.

4. The composition of claim 1 where the cationic germicidal agent comprises a quaternary ammonium compound selected from the group consisting of C$_{6-24}$ alkyl dimethyl benzyl ammonium chloride and C$_{6-24}$ alkyl dimethyl dichlorobenzyl ammonium chloride.

5. The composition of claim 1 wherein the water solubility imparting anion of the cationic germicidal agent, X$^-$, is selected from the group consisting of chloride, bromide, iodide, sulfate, and methyl sulfate.

6. The composition of claim 1 wherein the acid functional anionic polymer comprises a polymer of an ethylenically unsaturated carboxylic acid monomer.

7. The composition of claim 6 wherein the ethylenically unsaturated carboxylic acid polymer comprises monomers selected from the group consisting of methacrylic acid, acrylic acid, itaconic acid, aconitic acid, cinnamic acid, crotonic acid, mesaconic acid, carboxyethyl acrylic acid, maleic acid, and fumaric acid.

8. The composition of claim 6 wherein the ethylenically unsaturated carboxylic acid containing monomers additionally comprise an ethylenically unsaturated monomer selected from the group consisting of hydroxyethyl methacrylate, ethylene, propylene, isobutylene, vinyl chloride, vinyl acetate, styrene, and chlorostyrene.

9. The composition of claim 1 wherein the acid functional anionic polymer comprises monomers selected from the group consisting of vinyl benzene sulfonic acid, acrylamidoalkyl sulfonic acid, ethylenically unsaturated olefin sulfonic acid.

10. The composition of claim 1 additionally comprising an adjuvant.

11. The composition of claim 10 wherein the adjuvant is selected from the group consisting of a carboxymethyl cellulose, an alginic acid, a polycarboxyl acid polymer or salts thereof.

12. The composition of claim 10 wherein the adjuvant is selected from the group consisting of propylene glycol, butoxyethanol, or an alkyl glycol ether.

13. A single-part homogeneous, organic solvent-free, aqueous storage stable antimicrobial film-forming composition comprising:
(a) about 50 wt-% to 90 wt-% water;
(b) about 0.10 wt-% to 40 wt-% of a cationic germicidal agent compound having a structure (R) (R$_1$) (R$_2$) (R$_3$) N$^+$ X$^-$;

wherein R, R$_1$, R$_2$, and R$_3$ are independently selected from groups including benzyl, alkyl benzyl, halo benzyl, C$_{1-14}$ alkyl, C$_{5-24}$ alkyl or C$_{1-4}$ hydroxyl alkyl and X$^-$ represents an anion capable of imparting water solubility or dispersibility to the compound; and (c) about 0.10 wt-% to 35 wt-% of an ethylenically unsaturated carboxylic acid polymer comprising monomers selected from the group consisting of methacrylic acid, acrylic acid, itaconic acid, aconitic acid, cinnamic acids, crotonic acids, mesaconic acids, carboxyethyl acrylic acid, maleic acid, and fumaric acid, or combinations thereof, wherein said germicidal agent and anionic polymer remain dissolved in a homogeneous, organic solvent-free, aqueous solution until used and said homogeneous aqueous solution remains phase-stable without precipitation for an extended period of time.

14. The composition of claim 13 where the cationic germicidal agent comprises a quaternary ammonium compound selected from the group consisting of C$_{6-24}$ alkyl dimethyl benzyl ammonium chloride and C$_{6-24}$ alkyl dimethyl dichlorobenzyl ammonium chloride.

15. The composition of claim 13 wherein the ethylenically unsaturated carboxylic acid monomers additionally comprise an ethylenically unsaturated monomer selected from the group consisting of ethylene, propylene, isobutylene, vinyl chloride, vinyl acetate, styrene, and chlorostyrene.

16. The composition of claim 13 additionally comprising an adjuvant.

17. The composition of claim 16 wherein the adjuvant selected from the group consisting of a carboxymethyl cellulose, an alginic acid, a polycarboxyl acid polymer or salts thereof.

18. The composition of claim 16 wherein the adjuvant is selected from the group consisting of propylene glycol, 19. A single-part homogeneous, organic solvent-free, aqueous storage stable antimicrobial film-forming composition consisting essentially of:
(a) about 70 wt-% to 90 wt-% of water;
(b) about 10 wt-% to 25 wt-% of a cationic quaternary ammonium compound which is selected from the group consisting of C$_{6-24}$ alkyl dimethyl benzyl ammonium chloride and C$_{6-24}$ alkyl dimethyl dichlorobenzyl ammonium chloride, or combinations thereof, and
(c) about 6 wt-% to 25 wt-% of an ethylenically unsaturated carboxylic acid containing polymer comprising monomers selected from the group consisting of methacrylic acid, acrylic acid, itaconic acid, aconitic acid, cinnamic acids, crotonic acids, mesaconic acids, carboxyethyl acrylic acid, maleic acid, and fumaric acid, or combinations thereof, wherein said film-forming composition remains dissolved as a homogeneous, organic solvent-free, aqueous solution until used and said homogeneous aqueous solution remains phase-stable without precipitation for an extended period of time.

20. The composition of claim 19 wherein the ethylenically unsaturated carboxylic acid containing monomers additionally comprise an ethylenically unsaturated monomer selected from the group consisting of ethylene, propylene, isobutylene, vinyl chloride, vinyl acetate, styrene, and chlorostyrene.

21. The composition of claim 19 additionally comprising an adjuvant.

22. The composition of claim 21 wherein the adjuvant is selected from the group consisting of a carboxymethyl cellulose, an alginic acid, a polycarboxylic acid polymer or salts thereof.

23. The composition of claim 21 wherein the adjuvant is selected from the group consisting of propylene glycol, butoxyethanol, or an alkyl glycol ether.

24. A method of treating a surface with a single-part homogeneous, solvent-free, aqueous storage stable, antimicrobial film-forming composition, said film-forming composition comprising:
(a) a major portion of water;
(b) an antimicrobially effective amount of a cationic germicidal agent having the structure (R) (R$_1$) (R$_2$) (R$_3$) N$^+$ X$^-$ wherein R, R$_1$, R$_2$, and R$_3$ are independently selected from groups including benzyl, alkyl benzyl, halo benzyl, C$_{1-14}$ alkyl, C$_{5-24}$ alkyl or C$_{1-4}$ hydroxyl alkyl and X- represents an anion capable of imparting water solubility or dispersability to the compound; and
(c) a stoichemetrically effective amount of polymeric carboxylic acid
wherein said cationic germicidal agent and anionic polymer remain dissolved in a homogeneous aqueous solution until used, said method comprising the step of applying said film-forming composition to the intended surface of application.

25. The method of claim 24 wherein at least one of R, R$_1$, R$_2$, and R$_3$ moieties on the cationic germicidal agent is independently selected from the group consisting of methyl, ethyl, propyl, and butyl.

26. The method of claim 24 wherein at least one of R, R$_1$, R$_2$, and R$_3$ moieties of the cationic germicidal agent is independently selected from the group consisting of cycloalkyl groups, aryl groups, aryl alkyl groups, and high alkyl groups.

27. The method of claim 24 where the cationic germicidal agent comprises a quaternary ammonium compound selected from the group consisting of C$_{6-24}$ alkyl dimethyl benzyl ammonium chloride and C$_{6-24}$ alkyl dimethyl dichlorobenzyl ammonium chloride.

28. The method of claim 24 wherein the water solubility imparting anion of the cationic germicidal agent, X$^-$, is selected from the group consisting of chloride, bromide, iodide, sulfate, and methyl sulfate.

29. The method of claim 24 wherein the acid functional anionic polymer is a polymer of an ethylenically unsaturated carboxylic acid monomer.

30. The method of claim 24 wherein the ethylenically unsaturated carboxylic acid polymer comprises monomers selected from the group consisting of methacrylic acid, acrylic acid, itaconic acid, aconitic acid, cinnamic acid, crotonic acid, mesaconic acid, carboxyethyl acrylic acid, maleic acid, and fumaric acid.

31. The method of claim 30 wherein the ethylenically unsaturated carboxylic acid monomers additionally comprise an ethylenically unsaturated monomer selected from the group consisting of ethylene, propylene, isobutylene, vinyl chloride, vinyl acetate, styrene, and chlorostyrene.

32. The method of claim 24 wherein the acid functional anionic polymer comprises a polymer comprised of monomers selected from the group consisting of vinyl benzene sulfonic acid, acrylamidoalkyl sulfonic acid, ethylenically unsaturated olefin sulfonic acid.

33. The method of claim 24 wherein the aqueous, storage stable, antimicrobial film-forming composition additionally comprises an adjuvant.

34. The method of claim 33 wherein the adjuvant is selected from the group consisting of a carboxymethyl cellulose, an alginic acid, or a polycarboxylic acid polymer or salts thereof.

35. The method of claim 33 wherein the adjuvant is selected from the group consisting of propylene glycol, butoxyethanol, or an alkyl glycol ether.

36. A method of treating a surface with a single-part homogeneous, organic solvent-free, storage stale antimicrobial film-forming composition comprising:
(a) about 50 wt-% to 90 wt-% of water;
(b) about 0.10 wt-% to 35 wt-% of a germicidal agent having a structure (R) (R$_1$) (R$_2$) (R$_3$) N$^+$ X$^-$;
wherein R, R$_1$, R$_2$, and R$_3$ are independently selected from groups including benzyl, alkyl benzyl, halo benzyl, C$_{1-14}$ alkyl, C$_{5-24}$ alkyl or C$_{1-4}$ hydroxyalkyl and X$^-$ represents an anion capable of imparting water solubility or dispersibility to the compound; and
(c) about 0.10 wt-% to 35 wt-% of an ethylenically unsaturated carboxylic acid polymer comprising monomers selected from the group consisting of methacrylic acid, acrylic acid, itaconic acid, aconitic acid, cinnamic acids, crotonic acids, mesaconic acids, carboxyethyl acrylic acid, maleic acid, and fumaric acid, or combinations thereof,
wherein said cationic germicidal agent and said anionic polymer remain dissolved as a homogeneous, organic solvent free, aqueous solution until used and said homogeneous aqueous solution remains phase-stable without precipitation for an extended period of time, said method comprising the step of applying said film-forming composition to the intended surface of application.

37. The method of claim 36 where the cationic germicidal agent is selected from the group consisting of C$_{6-24}$ alkyl dimethyl benzyl ammonium chloride and C$_{6-24}$ alkyl dimethyl dichlorobenzyl ammonium chloride.

38. The method of claim 36 wherein the ethylenically unsaturated carboxylic acid monomers additionally comprise an ethylenically unsaturated monomer selected from the group consisting of ethylene, propylene, isobutylene, vinyl chloride, vinyl acetate, styrene, and chlorostyrene.

39. The method of claim 36 wherein the aqueous storage stable antimicrobial film-forming composition additionally comprising an adjuvant.

40. The method of claim 39 wherein the adjuvant is selected from the group consisting of a carboxymethylic cellulose, an alginic acid, or a polycarboxylic acid polymer or salts thereof.

41. The method of claim 39 wherein the adjuvant is selected from the group consisting of propylene glycol, butoxyethanol, or an alkyl glycol ether.

42. A method of treating a surface with a single-part homogeneous, organic solvent-free, aqueous storage stable antimicrobial film-forming composition consisting essentially of:
(a) about 70 wt-% to 90 wt-% of water;
(b) about 5 wt-% to 25 wt-% of a cationic quaternary ammonium compound selected from the group consisting of C$_{6-24}$ alkyl dimethyl benzyl ammonium chloride C$_{6-24}$ alkyl dimethyl dichlorobenzyl ammonium chloride and combinations thereof; and
(c) about 6 wt-% to 25 wt-% of an ethylenically unsaturated carboxylic acid polymer comprising monomers selected from the group consisting of methacrylic acid, acrylic acid, itaconic acid, aconitic acid, cinnamic acids, crotonic acids, mesaconic acids, carboxyethyl acrylic acid, maleic acid, fumaric acid, or combinations thereof, wherein said cationic quaternary ammonium compound and anionic polymer remain dissolved as a homogeneous, organic solvent free, aqueous solution until used and said homogeneous aqueous solution remains phase-stable without precipitation for an extended period of time, said method comprising the step of applying said film-forming composition to the intended surface of application.

43. The method of claim 42 wherein the ethylenically unsaturated carboxylic acid monomers additionally comprise an ethylenically unsaturated monomer selected from the group consisting of ethylene, propylene, isobutylene, vinyl chloride, vinyl acetate, styrene, and chlorostyrene.

44. The method of claim 42 wherein the aqueous storage stable antimicrobial film-forming composition additionally comprising an adjuvant.

45. The method of claim 44 wherein the adjuvant is selected from the group consisting of a carboxymethylic cellulose, an alginic acid, or a polycarboxylic acid polymer or salts thereof.

46. The method of claim 44 wherein the adjuvant is selected from the group consisting of propylene glycol, butoxyethanol, or an alkyl glycol ether.

* * * * *